US010825464B2

(12) United States Patent
Shi et al.

(10) Patent No.: US 10,825,464 B2
(45) Date of Patent: Nov. 3, 2020

(54) SUPPRESSION OF BREATH IN AUDIO SIGNALS (71) Applicant: Dolby Laboratories Licensing Corporation, San Francisco, CA (US)

(72) Inventors: Dong Shi, Shanghai (CN); David Gunawan, Sydney (AU); Glenn N. Dickins, Como (AU)

(73) Assignee: Dolby Laboratories Licensing Corporation, San Francisco, CA (US)

( * ) Notice: Subject to any disclaimer, the term of this patent is extended or adjusted under 35 U.S.C. 154(b) by 0 days.

(21) Appl. No.: 16/063,225

(22) PCT Filed: Dec. 15, 2016

(86) PCT No.: PCT/US2016/066844
§ 371 (c)(1),
(2) Date: Jun. 15, 2018

(87) PCT Pub. No.: WO2017/106454
PCT Pub. Date: Jun. 22, 2017

(65) Prior Publication Data
US 2018/0374496 A1 Dec. 27, 2018

Related U.S. Application Data (60) Provisional application No. 62/267,993, filed on Dec. 16, 2015.

(30) Foreign Application Priority Data

Dec. 16, 2015 (CN) .......................... 2015 1 0929705

(51) Int. Cl.
G10L 21/0264 (2013.01)
G10L 21/0208 (2013.01)
(Continued)

(52) U.S. Cl.
CPC ............ *G10L 21/0264* (2013.01); *A61B 7/00* (2013.01); *A61B 7/003* (2013.01);
(Continued)

(58) Field of Classification Search
CPC ............. G10L 21/0264; G10L 21/0232; G10L 21/0324; G10L 21/0208; G10L 25/21;
(Continued)

(56) References Cited

U.S. PATENT DOCUMENTS 6,351,529 B1  2/2002  Holeva
2003/0063024 A1  4/2003  Cerra
(Continued)

FOREIGN PATENT DOCUMENTS

WO  2008/081226  7/2008
WO  2014/045257  3/2014

OTHER PUBLICATIONS

Tiemounou, S. et al "Perception Based Automatic Classification of Background Noise in Super-wideband Telephony Document Thumbnail" JAES vol. 62, Issue 11, pp. 776-781, Nov. 2014.
(Continued)

*Primary Examiner* — Ping Lee (57) ABSTRACT

Example embodiments disclosed herein relate to audio signal processing. A method of processing an audio signal is disclosed. The method includes detecting, based on a power distribution of the audio signal, a type of content of a frame of the audio signal, generating a first gain based on a sound level of the frame for adjusting the sound level, processing the audio signal by applying the first gain to the frame; and in response to the type of content being detected to be a breath sound, generating a second gain for mitigating the breath sound and processing the audio signal by applying the second gain to the frame. Corresponding system and computer program product are also disclosed.

16 Claims, 5 Drawing Sheets

(51) Int. Cl.
  *G10L 25/21* (2013.01)
  *G10L 25/51* (2013.01)
  *H04M 3/56* (2006.01)
  *G10L 21/0324* (2013.01)
  *A61B 7/00* (2006.01)
  *G10L 21/0232* (2013.01)
(52) U.S. Cl.
  CPC ...... *G10L 21/0208* (2013.01); *G10L 21/0232* (2013.01); *G10L 21/0324* (2013.01); *G10L 25/21* (2013.01); *G10L 25/51* (2013.01); *H04M 3/568* (2013.01)
(58) Field of Classification Search
  CPC ........ G10L 25/51; H04M 3/568; A61B 7/003; A61B 7/00
  See application file for complete search history.

(56) References Cited

U.S. PATENT DOCUMENTS

| | | |
|---|---|---|
| 2003/0216908 A1 | 11/2003 | Berestesky |
| 2004/0230432 A1 | 11/2004 | Liu |
| 2006/0009970 A1 | 1/2006 | Harton |
| 2007/0173730 A1 | 7/2007 | Bikko |
| 2009/0012638 A1 | 1/2009 | Lou |
| 2010/0046770 A1 | 2/2010 | Chan |
| 2011/0069846 A1* | 3/2011 | Cheng .................... H04R 3/005 381/92 |
| 2011/0087079 A1 | 4/2011 | Aarts |
| 2011/0153321 A1 | 6/2011 | Allen |
| 2012/0157870 A1 | 6/2012 | Derkx |
| 2013/0022223 A1 | 1/2013 | Kehtarnavaz |
| 2013/0163781 A1 | 6/2013 | Thyssen |
| 2013/0342268 A1 | 12/2013 | Samuelsson |
| 2014/0155773 A1* | 6/2014 | Stamatopoulos ...... A61B 7/003 600/529 |

OTHER PUBLICATIONS

Ruinskiy, D. et al "An Effective Algorithm for Automatic Detection and Exact Demarcation of Breath Sounds in Speech and Song Signals" IEEE Transactions on Audio, Speech, and Language Processing, vol. 15, No. 3, Mar. 2007, pp. 838-850.
Lei, B. et al "Content-Based Classification of Breath Sound with Enhanced Features" Neurocomputing 141, pp. 139-147, Apr. 2014.
Archibald, Fitzgerald J "Automatic Level Controller for Speech Signals Using PID Controllers" Texas Instruments white Paper, SPRAAJ4—Jul. 2008.

* cited by examiner

SUPPRESSION OF BREATH IN AUDIO SIGNALS

TECHNOLOGY

Example embodiments disclosed herein generally relate to audio processing, and more specifically, to a method and system for mitigating unwanted breath sounds in audio signals.

BACKGROUND

In audio communication scenarios such as telecommunication or video conference, it is very common that breath sounds are also conveyed. Such breath sounds are normally unconscious and can be very loud especially when the mouth of a user is close to his/her microphone. This means the user is usually not aware of her/his own breath sound even the sound may be disturbing to other participants. In most cases, strong and long lasting breath sounds degrade the user experience. Therefore, it is desirable that there should be an intelligent system which can detect a disturbing breath sound and mitigate it so as to enhance the user experience.

SUMMARY

Example embodiments disclosed herein disclose a method and system for processing an audio signal in order to suppress the unwanted breath sound.

In one aspect, example embodiments disclosed herein provide a method of processing an audio signal. The method includes detecting, based on a power distribution of the audio signal, a type of content of a frame of the audio signal. Then the method generates a first gain based on a sound level of the frame for adjusting the sound level and processes the audio signal by applying the first gain to the frame. In response to the type of content being detected to be a breath sound, the method also includes generating a second gain for mitigating the breath sound and processing the audio signal by applying the second gain to the frame.

In another aspect, example embodiments disclosed herein provide a system for processing an audio signal. The system includes a type detector configured to detect, for a frame of the audio signal, a type of content of the frame based on a power distribution of the audio signal. The system also includes a gain generator configured to generate a first gain based on a sound level of the frame for adjusting the sound level and a processor configured to process the audio signal by applying the first gain to the frame. In response to the type of content being detected to be a breath sound, the gain generator being configured to generate a second gain for mitigating the breath sound and the processor being configured to process the audio signal by applying the second gain to the frame.

Through the following description, it would be appreciated that the type of the audio signal can be detected, and the audio signal can be processed accordingly if the type is the breath sound. The control can be configured to be intelligent and automatic. For example, in some cases when the breath sound is very loud, such a noise can be suppressed. On the other hand, if the breath sound does exist but not regarded as a loud and disturbing one, the level of such a noise can be maintained.

DESCRIPTION OF DRAWINGS

Through the following detailed descriptions with reference to the accompanying drawings, the above and other objectives, features and advantages of the example embodiments disclosed herein will become more comprehensible. In the drawings, several example embodiments disclosed herein will be illustrated in an example and in a non-limiting manner, wherein.

Throughout the drawings, the same or corresponding reference symbols refer to the same or corresponding parts.

DESCRIPTION OF EXAMPLE EMBODIMENTS

Principles of the example embodiments disclosed herein will now be described with reference to various example embodiments illustrated in the drawings. It should be appreciated that the depiction of these embodiments is only to enable those skilled in the art to better understand and further implement the example embodiments disclosed herein, not intended for limiting the scope in any manner.

In a telecommunication or video conference environment, several parties may be involved. During a speech of one speaker, other listeners normally keep silent for a long period. However, as a lot of speakers may wear their headsets in a way that the microphones are placed very close to their mouths, the breath sounds made by these listeners as they take breaths can be clearly captured and conveyed.

In such cases, if the breath sounds are already loud enough, other participants may feel uncomfortable with the noises. Otherwise, if the noises are not loud enough, some existing processing systems will automatically enhance the level of such noises gradually until they are loud enough because such systems simply adjust the level of whatever sound it processes if the sound is soft enough or loud enough. Eventually, the breath sounds are audible, and they lower the quality of communication.

Figure 1:
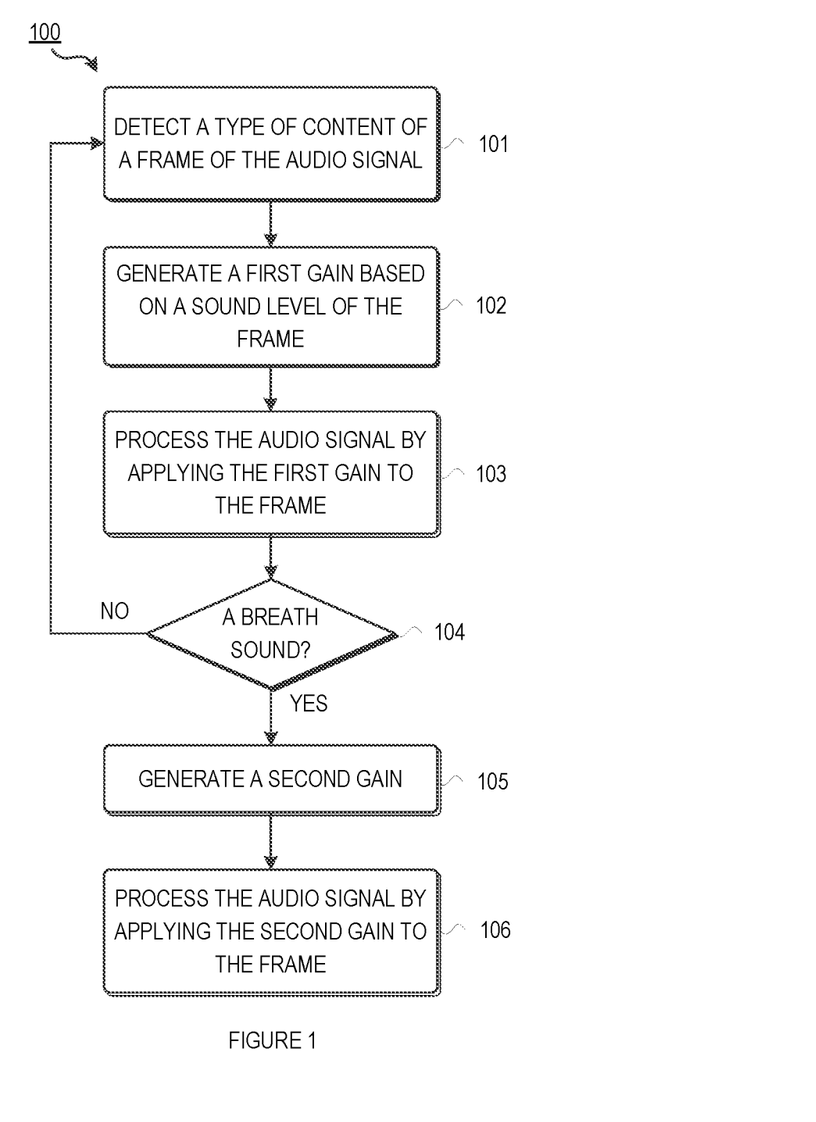
FIG. 1 illustrates a flowchart of a method of processing an audio signal in accordance with an example embodiment.

FIG. 1 illustrates a flowchart of a method 100 of processing a frame of an audio signal in accordance with an example embodiment. In general, content of the frame can be classified as breath sound or voice. The breath sound is further classified as "soft" breath if the sound level is smaller than a predefined threshold or "loud" breath if the sound level is greater than the predefined threshold. Then the frame can be processed depending on the classification of the content. In some embodiments, the method 100 can be applied to each frame of the audio signal.

In step 101, a type of content of a frame of an audio signal is detected based on a power distribution of the audio signal. The detection, for example in one example embodiment is carried out frame by frame. The input audio signal may for example, be captured by a microphone or any suitable audio capturing device or the like. The input audio signal may be an integrated signal after combining several signals captured from different users, or may be a signal captured from a single user prior to the combination with other captured audio signals. There can be several types such as breath and voice determined based on some metrics or criteria, so that the type can be assigned to the audio signal. Such metrics or criteria will be discussed in later paragraphs. As a result, the type of a particular frame of the audio signal can be determined as a breath sound, a voice sound or other kinds of sound, for example.

In step 102, a first gain is generated based on a sound level of the frame for adjusting the sound level. The audio signal is then processed by applying the generated first gain to the frame of the audio signal in 103, so that the adjusted frame of the audio signal will have an appropriate level heard by a listener. Thus, the first gain can be referred to as a levelling gain. Then, according to the detection result obtained in 101, if the type of content of the frame is classified in step 104 to be a breath sound, a second gain is further generated in step 105 for mitigating the breath sound. Otherwise, if the type of the frame is not regarded as a breath sound, the frame will be processed by applying the first gain only, and the type of a next frame is to be detected.

The second gain generated in 105 can be regarded as a suppression gain which is used to greatly mitigate the breath sounds so that the disturbing breath sounds made by the users are either removed or unnoticeable. The levelling gain is used to adjust the audio signal to an appropriate loudness for the listeners, while the suppression gain is used to largely reduce the loudness of the audio signal. For example, while the mitigation may suppress the sound level by over 30 dB if it is applied to the audio signal, the levelling operation may always applied to the audio signal to enhance a soft voice or decrease a loud voice until an appropriate sound level is reached, or remains unchanged if the sound level is already appropriate.

In step 106, the audio signal is processed by applying the second gain, in addition to the first gain, to the frame. The two gains altogether are contributed to output a signal, intentionally controlling the sound level of the audio signal. However, it is to be noted that neither of the two gains may be changed in some cases, while both of the two gains may be changed in some other cases.

Figure 2:
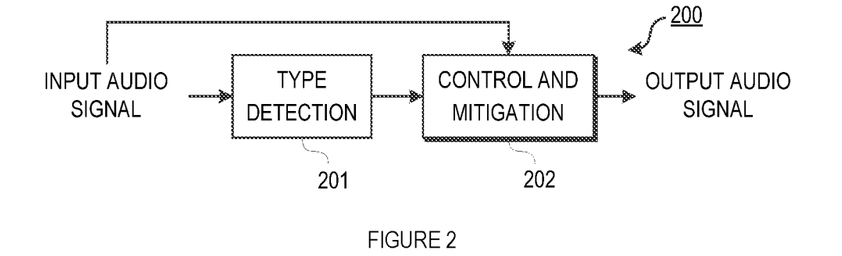
FIG. 2 illustrates a block diagram of processing the audio signal in accordance with an example embodiment.

FIG. 2 illustrates a block diagram of a system 200 showing how the input audio signal can be processed and converted to the output audio signal in accordance with an example embodiment. The input audio signal can be fed into both a type detection module 201 and a control and mitigation module 202. As discussed previously, the input audio signal is in some example embodiments, picked up by an audio capturing device, for example, a microphone mounted on a headset or an equivalent device or the like.

Typically, if the microphone is placed relatively close to the user's mouth or nose, his/her breath sounds may be picked up by the microphone with potentially extra noise that is caused by the air rubbing the surface of the microphone. The input audio signal is thus fed into the system 200 in a real time manner, usually in a frame by frame manner for audio processing. The type detection module 201 thus determines whether a breath sound exists in the current frame. The result is then fed into the control and mitigation module 202 that further changes behaviours of the system 200 in the presence of the breath sound. Depending on the logic in the control and mitigation module 202, the input signal is processed in a way that improves the overall user experience.

Figure 3:
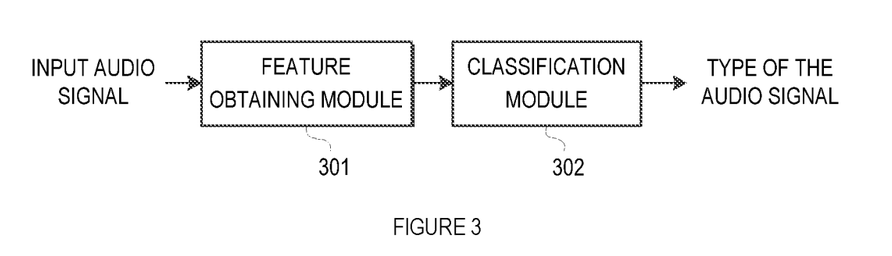
FIG. 3 illustrates a block diagram of detecting the type of the audio signal in accordance with an example embodiment.

The type detection module 201 can be further illustrated by FIG. 3, where the type of the audio signal can be detected. In the example embodiment shown in FIG. 3, the type detection module 201 may include a feature obtaining module 301 and a classification module 302.

In the feature obtaining module 301, the input audio signal can be transformed into multiple spaces, and different features representing the breath sound can be calculated. In practice, the input audio signal may contain various types of sounds, including voice, background noises and other nuisances (unwanted sounds other than the background noises) and the like. The features are chosen for differentiating the breath sound from voice sound.

Some metrics are useful for detecting breath sound by examining the features of the audio signal, and some features are listed in the following. Since there are different ways of obtaining the features, some non-limiting examples are listed and explained. It will be appreciated by those skilled in the art that the non-limiting examples listed are non-exhaustive and that there may be other features used for type detection. In one embodiment, the input audio signal is first transformed into the frequency domain and all of the features are calculated based on the frequency domain audio signal. Some example features will be described below.

In some example embodiment, the feature may include a spectral difference (SD) which indicates a difference in power between adjacent frequency bands. In one example embodiment, the SD may be determined by transforming the banded power values to logarithmic values after which these values are multiplied by a constant C (can be set to 10, for example) and squared. Each two adjacent squared results are subtracted each other for obtaining a differential value. Finally, the value of the SD is the median of the obtained differential values. This can be expressed as follows:

$$SD = \text{median}\left(\left(\text{diff}\left(C \cdot \log_{10}\begin{bmatrix} P_1 \\ P_2 \\ P_3 \\ \vdots \\ P_n \end{bmatrix}\right)\right)^2\right) \quad (1)$$

where $P_1 \ldots P_n$ represent the input banded power of the current frame (vectors are denoted in bold text, it is assumed to have n bands), the operation diff( ) represents a function that calculates the difference in power of two adjacent bands, and median( ) represents a function that calculates the median value of an input sequence.

In one embodiment, the input audio signal has a frequency response ranging from a lower limit to an upper limit, which can be divided into several bands such as for example, 0 Hz to 300 Hz, 300 Hz to 1000 Hz and 1000 Hz to 4000 Hz. Each band may, for example, be evenly divided into a number of bins. The banding structure can be any conventional ones such as equivalent rectangular banding, bark scale and the like.

The operation log in Equation (1) above, is used to differentiate the values of the banded power more clearly but it is not limited, and thus in some other examples, the operation log can be omitted. After obtaining the differences, these differences can be squared but this operation is not necessary as well. In some other examples, the operation median can be replaced by taking average and so forth.

Alternatively, or in addition, a signal to noise ratio (SNR) may be used to indicate a ratio of power of the bands to power of a noise floor, which can be obtained by taking the mean value of all the ratios of the banded power to the banded noise floor and transforming the mean values to logarithmic values which are finally multiplied by a constant:

$$SNR = C \cdot \log_{10}\left(\text{mean}\left(\begin{bmatrix} P_1/N_1 \\ P_2/N_2 \\ P_3/N_3 \\ \vdots \\ P_n/N_n \end{bmatrix}\right)\right) \quad (2)$$

where n represents the number of bands, $N_1 \ldots N_n$ represent the banded power of the noise floor in the input audio signal, and the operation mean[ ] represents a function that calculates the average value (mean) of an input sequence. In some example embodiments, the constant C may be set to 10.

$N_1 \ldots N_n$ can also be calculated using conventional methods such as minimum statistics or with prior knowledge of the noise spectra. Likewise, the operation log is used to differentiate the values more clearly but it is not limited, and thus in some other examples, the operation log can be omitted.

A spectral centroid (SC) indicates a centroid in power across the frequency range, which can be obtained by summing all the products of a probability for a frequency bin and the frequency for that bin:

$$SC = \begin{bmatrix} prob_1 & prob_2 & \ldots & prob_m \end{bmatrix} \begin{bmatrix} binfreq_1 \\ binfreq_2 \\ \vdots \\ binfreq_m \end{bmatrix} \quad (3)$$

where m represents the number of bins, $prob_1 \ldots prob_m$ each represents the normalized power spectrum calculated as prob=PB/sum(PB), in which the operation sum( ) represents a summation and PB represents a vector form of the power of each frequency bin (there are totally m bins). $binfreq_1 \ldots binfreq_m$ represent vector forms of the actual frequencies of all the m bins. The operation mean( ) calculates the average value or mean of the power spectrum.

It has been found that in some cases the majority of energy of the audio signal containing breath sounds lies more in the low frequency range. Therefore, by Equation (3) a centroid can be obtained, and if the calculated centroid for a current frame of the audio signal lies more in the low frequency range, the content of that frame has a higher chance to be a breath sound.

A spectral variance (SV) is another useful feature that can be used to detect the breath sound. The SV indicates a width in power across the frequency range, which can be obtained by summing the product of the probability for a bin and a square of the difference between a frequency for that bin and the spectral centroid for that bin. The SV is further obtained by calculating the square root of the above summation. An example calculation of SV can be expressed as follows:

$$SV = \sqrt{\begin{bmatrix} prob_1 & prob_2 & \ldots & prob_m \end{bmatrix} \begin{bmatrix} |binfreq_1 - SC|^2 \\ |binfreq_2 - SC| \\ \vdots \\ |binfreq_m - SC| \end{bmatrix}} \quad (4)$$

Alternatively, or in addition, a power difference (PD) is used as a feature for detection of breath. The PD indicates a change in power of the frame and an adjacent frame along time line, which can be obtained by calculating the logarithmic value of the sum of the banded power values for the current frame and the logarithmic value of the sum of the banded power values for the previous frame. After the logarithmic values are each multiplied by a constant (can be set to 10, for example), the difference is calculated in absolute value as the PD. The above processes can be expressed as:

$$PD = \left| C \cdot \log_{10}\sum_{i=1}^{n} P_i - C \cdot \log_{10}\sum_{i=1}^{n} LP_i \right| \quad (5)$$

where $LP_1 \ldots LP_n$ represent the banded power for the previous frame. PD indicates how fast the energy changes from one frame to another. For breath sounds, it is noted that the energy varies much slower than that of speech.

Another feature that can be used to detect the breath sound is band ratio (BR) which indicates a ratio of a first band and a second band of the bands, the first and second bands being adjacent to one another, which can be obtained by calculating ratios of one banded power to an adjacent banded power:

$$BR = \begin{bmatrix} P_2/P_1 \\ P_3/P_2 \\ \vdots \\ P_n/P_{n-1} \end{bmatrix} \quad (6)$$

In one embodiment, assuming there are bands span from 0 Hz to 300 Hz, 300 Hz to 1000 Hz and 1000 Hz to 4000 Hz, and only two BR will be calculated. It has been found that these ratios are useful for discriminating voiced frames from breath sounds.

In addition to these features measuring instantaneous values for the current time frame, their smoothed versions can be also calculated. For example, a simple first order recursive average can be used to calculate the smoothed versions by a weighted sum of a smoothed version of a particular feature for a previous time frame and an instantaneous value of the particular feature, where the sum of the weights is equal to 1:

$$y = a \cdot y(t-1) + (1-a) \cdot x \quad (7)$$

where y(t) represents the smoothed version of a particular feature (as mentioned above: SC, SD, PD and the like) for the current time frame t (and thus y(t−1) represents the smoothed version of the particular feature for the previous time frame), x(t) represents the instantaneous value of the particular feature, and a represents a constant smoothing factor having a typical value ranging from 0.8 to 0.95.

The classification module 302 classifies the frame as breath sound or voice based on one or more of the calculated features. Example embodiments in this regard will be described in the following paragraphs. For example, if half of the features fulfill predetermined thresholds, the probability of the frame of the audio signal being a nuisance is 50%. If all of the features fulfill the predetermined thresholds, the probability of the frame being a nuisance is very high, such as over 90%. More features being fulfilled result in a higher chance of the frame being a nuisance. As a result, if the probability is over a threshold according to some rules, the presence of the nuisance for the frame may be determined, and the classification module 302 may output a value "1" to indicate that the input audio signal includes a breath sound or output a value "0" if the input audio signal is not detected to contain such a breath sound. The classification can be implemented in various ways. Typical designs include heuristic rule based classifiers which combine the input features and transform them, usually in a nonlinear way, to an output (for example, value "0" or "1"). It can be regarded as a mapping function that maps an input feature vector to a discrete number of values, each representing the category/type of the signal. Those skilled in the art will appreciate that various popular classifiers may be employed such as support vector machine (SVM), adaptive boosting (AdaBoost), deep neural networks (DNN), decision trees and the like. Although a simple implementation of the classification module can be used based on heuristically designed rules, the type of the classification is not to be limited.

Figure 4:
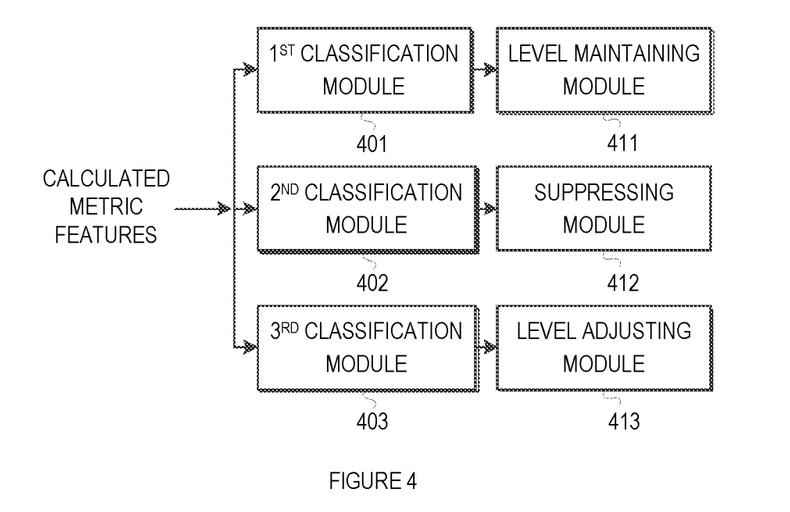
FIG. 4 illustrates a block diagram of a parallel classifying process in accordance with an example embodiment.

FIG. 4 illustrates a block diagram of a parallel classifying process in accordance with an example embodiment. In one embodiment, instead of incorporating just one classification module for the classification process as discussed above at one time, it is possible to use multiple classification modules to classify the audio signal of the current frame to examine whether it belongs to different groups simultaneously. In typical audio processing systems, there are multiple function blocks that perform different tasks, and the different needs of these blocks thus require different classification results. For example, as illustrated in the following embodiment, three classification modules are used for maintaining the sound level, controlling the mitigation (namely, to reduce the sound level greatly so that the user may not hear the sound) and controlling the levelling (namely, to slightly adjust the sound level in a relatively small range).

In one embodiment, a first classification module 401 used for maintaining level can be optimized for soft breath sounds that (when the classification module 302 outputs a value "0" for example, as discussed above) will otherwise result in the amplification of the signal by the subsequent processing system. A level maintaining module 411 can be used to maintain a gain for controlling the levelling so that the sound level of the signal will at least not be amplified. A second classification module 402 can be optimized for loud breath sounds (when the classification module 302 outputs a value "1" for example, as discussed above) that usually pass through the system without being attenuated. A suppressing module 412 can be used to mitigate the signal so that the breath sound is not audible. A third classification module 403 can be used to judge whether the sound belongs to a voice sound rather than a breath sound. For example, the third classification module 403 may output a value "2" to indicate that the signal contains a voice sound but not a breath sound. Then, a level adjusting module 413 can be used to adjust the level of the signal so that the voice sound has a proper volume. It is clear that the designs of the classification modules are coupled and tied to the specific functionalities of the overall audio processing system.

It should be noted that more or less classification modules are possible, with each module being optimized for one purpose. As such, the number of classification modules shown in FIG. 4 is merely a non-limiting example. In addition, the multiple classification modules functioning simultaneously are beneficial as they process and finish the classification tasks rapidly. The mitigation or suppression can be done by applying a suppression gain to the audio signal. By the suppression gain, the sound level of the audio signal for a particular frame can be dramatically decreased, for example, by a value of 30 dB or greater compared with a previous frame. This suppression gain is used to "mute" the audio signal if it is detected to be a loud breath which is usually considered as disturbing. On the other hand, the levelling control can be done by applying a levelling gain to the audio signal. By the levelling gain, the sound level of the audio signal for a particular frame can vary slightly, for example, within a range of ±10 dB. In one situation, this levelling gain is used to keep the sound level of the audio signal if it is detected to be a soft breath as defined previously by maintaining the levelling gain with respect to a previous frame. In another situation, the levelling gain is used to slightly increase the sound level if the audio signal is detected to be a voice sound and not loud enough (smaller than a predefined threshold), and to slightly decrease the sound level if the voice sound is too loud (larger than another predefined threshold). The suppression gain as well as the levelling gain can be applied altogether to the audio signal.

It is discussed in the following how the suppression gain and the levelling gain are applied to the audio signal by reference to FIG. 5, which illustrates a block diagram of applying a suppression gain s(t) and a levelling gain g(t) to the input audio signal in accordance with an example embodiment. Because two gains are both applied to the audio signal, the suppression gain can be regarded as a second gain for mitigating the breath sound, while the levelling gain can be regarded as a first gain for adjusting the sound level.

A type detection module 501 can be similar to the type detection module 201 as illustrated in FIG. 2, which will not be detailed again. In this embodiment, a breath suppression module 502 is used to control the suppression gain s(t) for the current frame t in case that the type detection module 501 outputs a value (in an example embodiment, a value "1" can be assigned to a classification result indicating that the detected audio signal for the particular frame is a loud breath sound) indicating the input audio signal belongs to a loud breath sound that is disturbing and preferred to be mitigated. The suppression gain s(t) is normally very small so that the input audio signal applied with the suppression gain s(t) will become very small (in an example embodiment, the suppression gain may decrease the sound level by at least 30 dB), making the output audio signal inaudible or unnoticeable.

A levelling control module 503 can be used to control the levelling gain g(t) for the current frame t in case that the type detection module 501 outputs a value indicating the input audio signal belongs to a soft breath sound (in an example embodiment, a value "0" can be assigned to a classification result indicating that the detected audio signal for the particular frame is a soft breath sound) or a voice sound (in an example embodiment, a value "2" can be assigned to a classification result indicating that the detected audio signal for the particular frame is a voice sound). If the input audio signal is a soft breath sound, the levelling gain g(t) can be maintained. Alternatively, a limit can be set for the levelling gain g(t) so that it would not exceed the limit. If the input audio signal is a voice sound, the levelling gain g(t) can be adjusted in accordance with the sound level of the voice sound.

In the levelling control module 503, the power of the input audio signal will be calculated. Ideally, if the input is voice sound only, then the levelling control module 503 generates the levelling gain g(t) that is used to multiply with the input audio signal. The resultant output audio signal will then be amplified (if the voice sound is too low) or attenuated (if the voice sound is too loud). In one embodiment, since the levelling gain g(t) is usually designed in a way that gradually approaches the desired gain, the change of the levelling gain g(t) can be maintained if the type detection module 501 outputs a value "0" or "1" for example. With the additional detection result, the suppression gain g(t) can be updated by adding the value of the levelling gain of a previous frame to a product of a change of the levelling gain towards a desired gain and an absolute value of an input detection result subtracted by 1:

$$g(t)=g(t-1)+d(t)\cdot|c_L(t)-1| \quad (8)$$

where d(t) represents the change of the gain towards the desired gain if the signal is a voice sound, $c_L(t)$ represents the input detection result which can be a value "1" if the audio signal for the current frame is detected to be a breath sound (no matter a soft breath sound or a loud breath sound), and t represents the frame number.

Equation (8) maintains the change of the levelling gain g(t) when there is detected to contain a breath sound, namely, the levelling gain for the current frame is equal to the levelling gain for the previous frame. This prevents the breath sound from being amplified and degrading the listening experience consequently.

Figure 5:
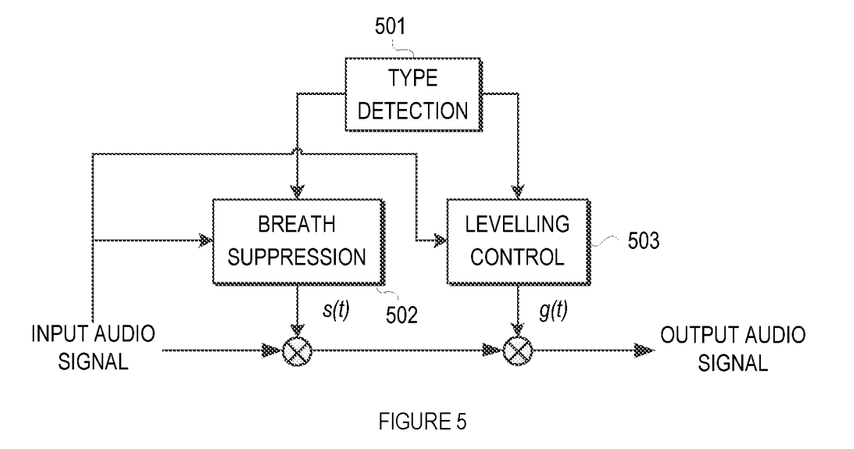
FIG. 5 illustrates a block diagram of applying a suppression gain and a levelling gain to the input audio signal in accordance with an example embodiment.
Figure 6:
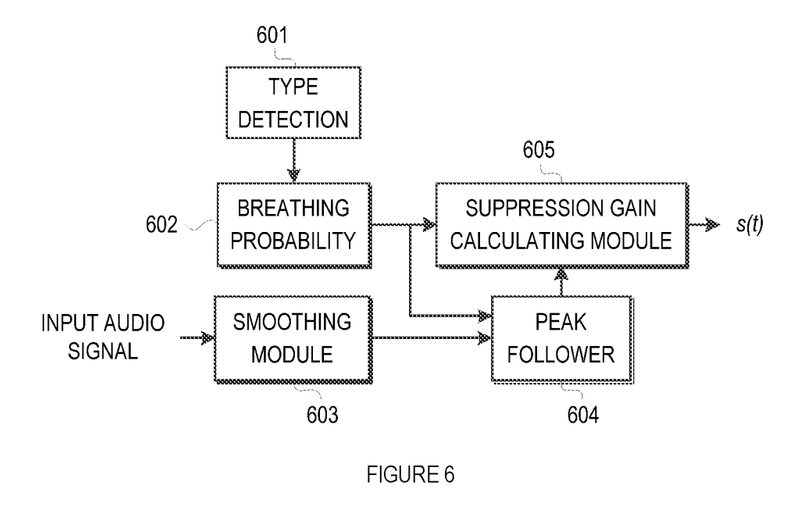
FIG. 6 illustrates a block diagram of generating the suppression gain in accordance with an example embodiment.

FIG. 6 illustrates a block diagram showing the logic in the breath suppression module 502, and a type detection module 601 can correspond to the type detection module 501 as illustrated in FIG. 5 and thus details are omitted. As discussed above, the output of the type detection module 601 is used to calculate the probability of the audio signal being a breath sound at a breathing probability module 602. The estimated probability that the current signal is a breath sound, denoted as $b_p(t)$, differs from the output of the type detection module 601 in that $b_p(t)$ is a smoothed version of the output of the type detection module 601 $c_s(t)$. $c_s(t)$ can be noisy and can vary from frame to frame but $b_p(t)$ becomes smoother. Using a smoothed version of $c_s(t)$ makes the system more robust against false classifications, i.e., signals misclassified as breath sounds. In one embodiment, $b_p(t)$ can be given by adding the smoothed output $b_p$ for a previous frame multiplied by a smoothing factor to the output $c_s$ for the current frame multiplied by 1 minus the smoothing factor:

$$b_p(t)=\alpha_p b_p(t-1)+(1-\alpha_p)c_s(t) \quad (9)$$

where $\alpha_p$ represents the smoothing factor. In one embodiment, the soothing factor can range from 0.8 to 0.9.

Equation (9) results in $b_p(t)$ increasing if there is a continuous breath sound and decreasing otherwise. $b_p(t)$ is further used to update both the suppression gain s(t) at a suppression gain calculating module 605 and a peak follower 604 of the input signal, respectively. Let $b_s(t)$ denote the suppression depth for the current frame. Typically $b_s(t)$ has a value between 0 and 1 and can be updated in the following way by applying $b_s$ for a previous frame added or subtracted by a predefined constant:

$$b_s(t) = \begin{cases} b_s(t-1)+\delta, & \text{if } b_p(t) > TH_b \\ b_s(t-1)-\delta, & \text{if } b_p(t) < TH_v \end{cases} \quad (10)$$

where $\delta$, $TH_b$ and $TH_v$ represent: predefined constants (representing the small increment), thresholds for increasing the suppression depth and decreasing the suppression depth, respectively. The suppression depth is here defined as a value between 0 and 1, while 0 being 0% suppression (no suppression) and 1 being applying 100% of the suppression gain. Equation (10) indicates that $b_s(t)$ is only updated when $b_p(t)$ is within a certain range, making the system more robust against noise.

On the other hand, $b_p(t)$ is also used to update the peak power follower of the breath sound. The peak follower 604 is an estimate of the power (of how loud the breath sound is) follows the loudest frames within a breathing period. It is used together with $b_s(t)$ to calculate the final suppression gain s(t). Let $p_{pk}(t)$ denote the estimated peak energy of the breath sound, and $p_{pk}(t)$ can be updated by choosing either $p_{pk}$ for a previous frame multiplied by a smoothing factor for peak decay, or a sum of $p_{pk}$ for the previous frame multiplied by the smoothing factor for peak decay and a logarithmic value of input power for the current frame multiplied by 1 minus a short term smoothing factor:

$$p_{pk}(t) = \begin{cases} \max(\alpha_{pk} p_{pk}(t-1), \alpha_s p_{pk}(t-1) + (1-\alpha_s)p(t)), & \text{if } b_p(t) > TH_b \\ \alpha_{pk} p_{pk}(t-1), & \text{otherwise} \end{cases} \quad (11)$$

where $\alpha_{pk}$, $\alpha_s$ and p(t) represent the smoothing factor for peak decay, the short term smoothing factor and the logarithmic value of input power for the current frame, respectively. $\alpha_{pk}$ can be set to a value close to 1 (0.999 for example) whereas $\alpha_s$ can be a value much smaller than 1 (0.40 for example). The smoothing process can be done at a smoothing module 603. The Equation (11) simply ensures that the value of the peak follower 604 does not decrease too quickly. The final suppression gain s(t) is then given by 10 to the power of $b_s(t)$ multiplied by either a value "0" or a predefined constant specifying the minimum power of the sound needs to be suppressed minus $p_{pk}(t)$:

$$s(t)=10^{b_s(t)*\min(0,(P_T-p_{pk}(t)))} \quad (12)$$

where $P_T$ represents the pre-defined constant specifying the minimum power of the sound needs to be suppressed if the signal is a breath sound, with its typical value ranged from −60 to −40.

The final output audio signal is then multiplied by both s(t) and g(t) as shown in FIG. 5. Consequently, in an example experiment, a waveform of a processed audio signal can be shown in FIG. 7B in accordance with an example embodiment compared with an unprocessed audio signal shown in FIG. 7A.

Figure 7A:
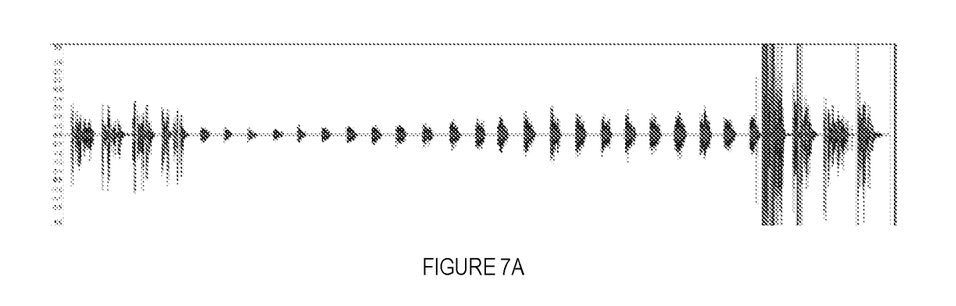
FIG. 7 illustrates a waveform of a processed audio signal in accordance with an example embodiment compared with an unprocessed audio signal.
Figure 7B:
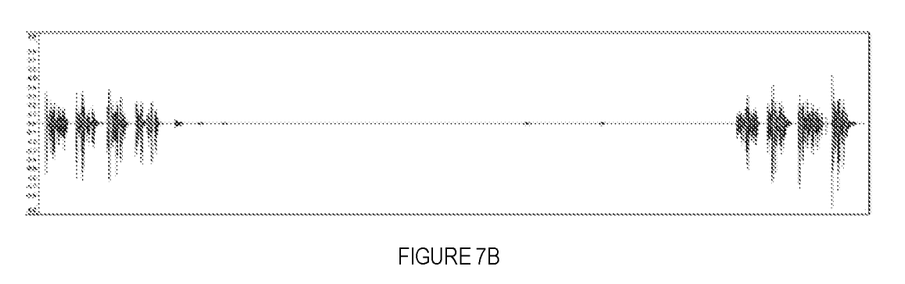

FIG. 7A shows the output of the system in response to a "speech+breath+speech" clip without a breath control while FIG. 7B shows the output with a breath control in accordance with the example embodiments described herein. It is observed that, without the breath control, the breath sound gradually increases over time (seen from the increase in the power of the breath sound). This causes the level of the second speech section too loud. Moreover, the unsuppressed breath sounds are somewhat annoying. In comparison, with the breath control, the disturbing breath sound can be effectively suppressed or mitigated when there is no voice sound conveyed, and the level of the second speech section is adequate.

Figure 8:
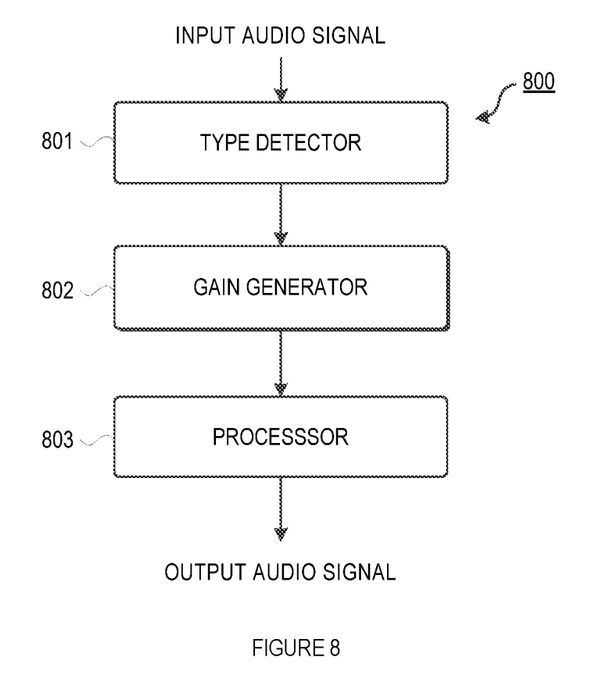
FIG. 8 illustrates a system for processing an audio signal in accordance with an example embodiment.

FIG. 8 illustrates a system 800 for processing an audio signal in accordance with an example embodiment. As shown, the system 800 includes a type detector 801 configured to detect, for a frame of the audio signal, a type of content of the frame based on a power distribution of the audio signal. The system also includes a gain generator 802 configured to generate a first gain based on a sound level of the frame for adjusting the sound level and a processor 803 configured to process the audio signal by applying the first gain to the frame. In response to the type of content being detected to be a breath sound, the gain generator 802 is configured to generate a second gain for mitigating the breath sound and the processor 803 is configured to process the audio signal by applying the second gain to the frame.

In an example embodiment, the type detector 801 may include a feature obtainer configured to obtain a feature based on the power distribution of the audio signal and a classifier configured to classify the type of content of the frame based on the feature.

In an further example embodiment, the frame includes a plurality of bands covering a frequency range, and the feature is selected from a group consisted of: a spectral difference indicating a difference in power between adjacent bands, a signal to noise ratio (SNR) indicating a ratio of power of the bands to power of a noise floor, a spectral centroid indicating a centroid in power across the frequency range; a spectral variance indicating a width in power across the frequency range, a power difference indicating a change in power of the frame and an adjacent frame and a band ratio indicating a ratio of a first band and a second band of the bands, the first and second bands being adjacent to one another.

In yet another example embodiment, in response to the type of content being detected to be a breath sound, the system 800 may further include a second gain controller configured to update, in response to the sound level of the frame exceeding a threshold, a value of the second gain so that the sound level of the audio signal for a current frame is reduced by a predefined first value with regard to a previous frame.

In one another example embodiment, in response to the type of content being detected to be a breath sound, the system 800 may further include a first gain controller configured to update, in response to the sound level of the frame being below the threshold, a value of the first gain so that the sound level of the audio signal for a current frame is maintained with regard to a previous frame.

In a further example embodiment, the first gain controller is further configured to update, in response to the type of the input audio signal being detected to be the voice sound, a value of the first gain so that the sound level of the audio signal for a current frame is changed by a predefined second value with regard to a previous frame.

For the sake of clarity, some additional components of the system 800 are not shown in FIG. 8. However, it should be appreciated by those skilled in the art that the features as described above with reference to FIGS. 1-7 are all applicable to the system 800. Moreover, the components of the system 800 may be a hardware module or a software unit module. For example, in some embodiments, the system 800 may be implemented partially or completely with software and/or firmware, for example, implemented as a computer program product embodied in a computer readable medium. Alternatively or additionally, the system 800 may be implemented partially or completely based on hardware, for example, as an integrated circuit (IC), an application-specific integrated circuit (ASIC), a system on chip (SOC), a field programmable gate array (FPGA), and so forth. The scope of the present disclosure is not limited in this regard.

Figure 9:
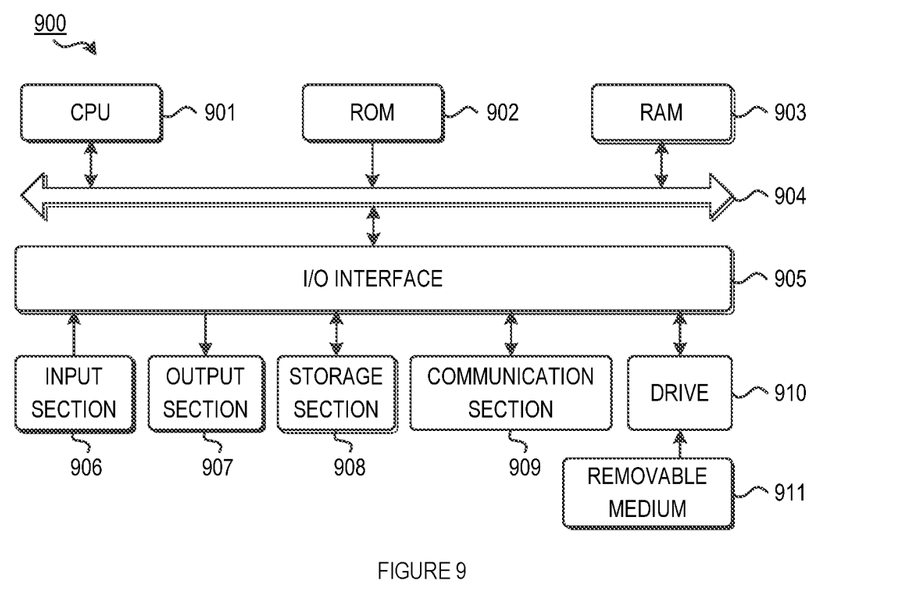
FIG. 9 illustrates a block diagram of an example computer system suitable for the implementing example embodiments disclosed herein.

FIG. 9 shows a block diagram of an example computer system 900 suitable for implementing example embodiments disclosed herein. As shown, the computer system 900 comprises a central processing unit (CPU) 901 which is capable of performing various processes in accordance with a program stored in a read only memory (ROM) 902 or a program loaded from a storage section 908 to a random access memory (RAM) 903. In the RAM 903, data required when the CPU 901 performs the various processes or the like is also stored as required. The CPU 901, the ROM 902 and the RAM 903 are connected to one another via a bus 904. An input/output (I/O) interface 905 is also connected to the bus 904.

The following components are connected to the I/O interface 905: an input section 906 including a keyboard, a mouse, or the like; an output section 907 including a display, such as a cathode ray tube (CRT), a liquid crystal display (LCD), or the like, and a speaker or the like; the storage section 908 including a hard disk or the like; and a communication section 909 including a network interface card such as a LAN card, a modem, or the like. The communication section 909 performs a communication process via the network such as the internet. A drive 910 is also connected to the I/O interface 905 as required. A removable medium 911, such as a magnetic disk, an optical disk, a magneto-optical disk, a semiconductor memory, or the like, is mounted on the drive 910 as required, so that a computer program read therefrom is installed into the storage section 908 as required.

Specifically, in accordance with the example embodiments disclosed herein, the processes described above with reference to FIGS. 1-7 may be implemented as computer software programs. For example, example embodiments disclosed herein comprise a computer program product including a computer program tangibly embodied on a machine readable medium, the computer program including program code for performing methods 100. In such embodiments, the computer program may be downloaded and mounted from the network via the communication section 909, and/or installed from the removable medium 911.

Generally speaking, various example embodiments disclosed herein may be implemented in hardware or special purpose circuits, software, logic or any combination thereof. Some aspects may be implemented in hardware, while other aspects may be implemented in firmware or software which may be executed by a controller, microprocessor or other computing device. While various aspects of the example embodiments disclosed herein are illustrated and described as block diagrams, flowcharts, or using some other pictorial representation, it will be appreciated that the blocks, apparatus, systems, techniques or methods described herein may be implemented in, as non-limiting examples, hardware, software, firmware, special purpose circuits or logic, general purpose hardware or controller or other computing devices, or some combination thereof.

Additionally, various blocks shown in the flowcharts may be viewed as method steps, and/or as operations that result from operation of computer program code, and/or as a plurality of coupled logic circuit elements constructed to carry out the associated function(s). For example, example embodiments disclosed herein include a computer program product comprising a computer program tangibly embodied on a machine readable medium, the computer program containing program codes configured to carry out the methods as described above.

In the context of the disclosure, a machine readable medium may be any tangible medium that can contain, or store a program for use by or in connection with an instruction execution system, apparatus, or device. The machine readable medium may be a machine readable signal medium or a machine readable storage medium. A machine readable medium may include, but not limited to, an electronic, magnetic, optical, electromagnetic, infrared, or semiconductor system, apparatus, or device, or any suitable combination of the foregoing. More specific examples of the machine readable storage medium would include an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing.

Computer program code for carrying out methods of the present disclosure may be written in any combination of one or more programming languages. These computer program codes may be provided to a processor of a general purpose computer, special purpose computer, or other programmable data processing apparatus, such that the program codes, when executed by the processor of the computer or other programmable data processing apparatus, cause the functions/operations specified in the flowcharts and/or block diagrams to be implemented. The program code may execute entirely on a computer, partly on the computer, as a stand-alone software package, partly on the computer and partly on a remote computer or entirely on the remote computer or server or distributed among one or more remote computers or servers.

Further, while operations are depicted in a particular order, this should not be understood as requiring that such operations be performed in the particular order shown or in a sequential order, or that all illustrated operations be performed, to achieve desirable results. In certain circumstances, multitasking and parallel processing may be advantageous. Likewise, while several specific implementation details are contained in the above discussions, these should not be construed as limitations on the scope of any disclosure or of what may be claimed, but rather as descriptions of features that may be specific to particular embodiments of particular disclosures. Certain features that are described in this specification in the context of separate embodiments can also be implemented in combination in a single embodiment. Conversely, various features that are described in the context of a single embodiment can also be implemented in multiple embodiments separately or in any suitable subcombination.

Various modifications, adaptations to the foregoing example embodiments of this disclosure may become apparent to those skilled in the relevant arts in view of the foregoing description, when read in conjunction with the accompanying drawings. Any and all modifications will still fall within the scope of the non-limiting and example embodiments of this disclosure. Furthermore, other example embodiments set forth herein will come to mind of one skilled in the art to which these embodiments pertain to having the benefit of the teachings presented in the foregoing descriptions and the drawings.

What is claimed is:

1. A method of processing an audio signal, comprising:
   detecting, based on a power distribution of the audio signal in a frequency range, a type of content of a frame of the audio signal;
   generating a first gain based on a sound level of the frame for adjusting the sound level;
   processing the audio signal by applying the first gain to the frame;
   determining, based at least in part on a location of a centroid in the power distribution of the audio signal, whether the detected type of content of the frame of the audio signal is a breath sound; and
   in response to determining, based at least in part on a location of a centroid in the power distribution of the audio signal, that the detected type of content is a breath sound, performing:
      generating a second gain for suppressing the breath sound; and
      processing the audio signal by applying the second gain to the frame.

2. The method according to claim 1, wherein detecting the type of content of the frame comprises:
   obtaining a feature based on the power distribution of the audio signal; and
   classifying the type of content of the frame based on the feature.

3. The method according to claim 2, wherein the frame includes a plurality of bands covering the frequency range, and the feature comprises at least one of:
   a spectral difference indicating a difference in power between adjacent bands;
   a signal to noise ratio (SNR) indicating a ratio of power of the bands to power of a noise floor;
   a spectral centroid indicating a centroid in power across the frequency range;
   a spectral variance indicating a width in power across the frequency range;
   a power difference indicating a change in power of the frame and an adjacent frame; or
   a band ratio indicating a ratio of a first band and a second band of the bands, the first and second bands being adjacent to one another.

4. The method according claim 1, comprising: in response to the type of content being detected to be a breath sound:
   in response to the sound level of the frame exceeding a threshold, updating a value of the second gain so that the sound level of the audio signal for a current frame is reduced by a predefined first value with regard to a previous frame, or
   in response to the sound level of the frame being below the threshold, updating a value of the first gain so that the sound level of the audio signal for a current frame is maintained with regard to a previous frame.

5. The method according to any of claim 1, further comprising:
   in response to the type of content of the audio signal being detected to be a voice sound, updating a value of the first gain so that the sound level of the audio signal for a current frame is changed by a predefined second value with regard to a previous frame.

6. A system for processing an audio signal, including:
   a type detector configured to detect, for a frame of the audio signal, a type of content of the frame based on a power distribution of the audio signal in a frequency range;
   a gain generator configured to generate a first gain based on a sound level of the frame for adjusting the sound level; and a processor configured to process the audio signal by applying the first gain to the frame;

wherein the type detector configured to determine, based at least in part on a location of a centroid in the power distribution of the audio signal, whether the detected type of content of the frame of the audio signal is a breath sound;

wherein, in response to determining, based at least in part on a location of a centroid in the power distribution of the audio signal, that the type of content is a breath sound:

the gain generator generates a second gain for suppressing the breath sound; and the processor processes the audio signal by applying the second gain to the frame.

7. The system according to claim 6, wherein the type detector includes:

a feature obtainer configured to obtain a feature based on the power distribution of the audio signal; and a classifier configured to classify the type of content of the frame based on the feature.

8. The system according to claim 7, wherein the frame includes a plurality of bands covering the frequency range, and the feature comprises at least one of:

a spectral difference indicating a difference in power between adjacent bands;

a signal to noise ratio (SNR) indicating a ratio of power of the bands to power of a noise floor;

a spectral centroid indicating a centroid in power across the frequency range;

a spectral variance indicating a width in power across the frequency range;

a power difference indicating a change in power of the frame and an adjacent frame; or a band ratio indicating a ratio of a first band and a second band of the bands, the first and second bands being adjacent to one another.

9. The system according to claim 6, wherein the system further includes:

a second gain controller configured to, in response to the type of content being detected to be a breath sound and in response to the sound level of the frame exceeding a threshold, update a value of the second gain so that the sound level of the audio signal for a current frame is reduced by a predefined first value with regard to a previous frame.

10. The system according to any claim 6, wherein the system further includes:

a first gain controller configured to update, in response to the type of content being detected to be a breath sound and in response to the sound level of the frame being below a threshold, a value of the first gain so that the sound level of the audio signal for a current frame is maintained with regard to a previous frame.

11. The system according to claim 10, wherein the first gain controller is further configured to update, in response to the type of the audio signal being detected to be a voice sound, a value of the first gain so that the sound level of the audio signal for a current frame is changed by a predefined second value with regard to a previous frame.

12. A non-transient computer-readable medium storing instructions which, when executed by a processor, cause the processor to perform operations comprising:

detecting, based on a power distribution of an audio signal in a frequency range, a type of content of a frame of the audio signal;

generating a first gain based on a sound level of the frame for adjusting the sound level;

processing the audio signal by applying the first gain to the frame;

determining, based at least in part on a location of a centroid in the power distribution of the audio signal, whether the detected type of content of the frame of the audio signal is a breath sound; and in response to determining, based at least in part on a location of a centroid in the power distribution of the audio signal, that the detected type of content is a breath sound, performing:

generating a second gain for suppressing the breath sound; and processing the audio signal by applying the second gain to the frame.

13. The non-transitory computer-readable medium according to claim 12, wherein detecting the type of content of the frame comprises:

obtaining a feature based on the power distribution of the audio signal; and classifying the type of content of the frame based on the feature.

14. The non-transitory computer-readable medium according to claim 13, wherein the frame comprises a plurality of bands covering the frequency range, and the feature comprises at least one of:

a spectral difference indicating a difference in power between adjacent bands;

a signal to noise ratio (SNR) indicating a ratio of power of the bands to power of a noise floor;

a spectral centroid indicating a centroid in power across the frequency range;

a spectral variance indicating a width in power across the frequency range;

a power difference indicating a change in power of the frame and an adjacent frame; or a band ratio indicating a ratio of a first band and a second band of the bands, the first and second bands being adjacent to one another.

15. The non-transitory computer-readable medium according to claim 12, the operations comprising: in response to the type of content being detected to be a breath sound:

in response to the sound level of the frame exceeding a threshold, updating a value of the second gain so that the sound level of the audio signal for a current frame is reduced by a predefined first value with regard to a previous frame, or in response to the sound level of the frame being below the threshold, updating a value of the first gain so that the sound level of the audio signal for a current frame is maintained with regard to a previous frame.

16. The non-transitory computer-readable medium according to claim 12, the operations comprising:

in response to the type of content of the audio signal being detected to be a voice sound, updating a value of the first gain so that the sound level of the audio signal for a current frame is changed by a predefined second value with regard to a previous frame.

* * * * *